United States Patent [19]

Day et al.

[11] Patent Number: 4,548,754

[45] Date of Patent: Oct. 22, 1985

[54] ESTERIFICATION OF WAX OXIDATES

[75] Inventors: Frederic F. Day; William J. Powers, III; Eric D. Ewen; Gerald L. Piper, all of Port Arthur, Tex.

[73] Assignee: Texaco Inc., White Plains, N.Y.

[21] Appl. No.: 525,844

[22] Filed: Aug. 24, 1983

[51] Int. Cl.$^4$ ................................................ C11C 3/02
[52] U.S. Cl. .................................................. 260/410.9 R
[58] Field of Search ..................................... 260/410.9 R

[56] References Cited

U.S. PATENT DOCUMENTS 4,065,418 12/1977 Foulks, Jr. et al. ............ 260/410.9 R Primary Examiner—Anton H. Sutto
Attorney, Agent, or Firm—Robert A. Kulason; Jack H. Park; Richard A. Morgan

[57] ABSTRACT

A method for esterifying an unsweated, oil containing wax oxidate includes the use of an alcohol such as methanol and an organic sulfonic acid such as methane sulfonic acid. The use of methane sulfonic acid results in the clean separation of the ester from water which is used to wash the acid catalyst from the ester after esterification. Previously, the use of a strong mineral acid such as sulfuric acid resulted in an emulsion forming after the esterification of an unsweated oil containing wax oxidate.

11 Claims, No Drawings

4,548,754

ESTERIFICATION OF WAX OXIDATES

BACKGROUND OF THE INVENTION

This invention relates to the esterification of an unsweated wax oxidate and more particularly, to the use of an organic sulfonic acid as an esterification catalyst for use with the unsweated wax oxidate.

Esters of petroleum wax oxidates have found uses in various formulations, one of which is as a corrosion inhibitor.

Previously, the wax oxidate esters were made by the mineral acid catalyzed esterification of wax oxidates with an alcohol, such as methanol. Generally, the petroleum wax oxidates used for the formation of such esters were of the sweated or deoiled type.

Petroleum waxes used for the formation of wax oxidates and subsequently for the esters are obtained through various dewaxing procedures of crude oil fractions, such as solvent dewaxing. Such waxes after being removed from the crude oil fraction can contain upwards of 15 percent by weight, generally 5 to 15 percent by weight oil. The oil can be removed by a sweating or deoiling process which involves the slow heating of a solid mass of oil containing wax. Such heating causes the waxes with the lowest melting points to melt and to dissolve into the oil that is present as free oil between the wax crystals. This increase in the liquid content of the solid mass eventually reaches a level wherein the liquid can no longer remain absorbed between the wax crystals and then the oil separates from the solid mass of wax. The process is continued until a wax having a desired low oil content is achieved.

The soiling or sweating process adds to the expense and handling required of the wax prior to its formation into the desired ester and thus, it would be desirable to eliminate such a deoiling step. However, when an oil containing wax was subjected to air oxidation and subsequent esterification with the generally used sulfuric acid, the ester resulting therefrom was not acceptable, since when an attempt to remove the sulfuric acid from the ester by water washing was made, an emulsion formed which was difficult to separate. Such emulsion formation did not usually occur when deoiled wax was used for the oxidation and esterification process.

A process for the oxidation of waxes in the presence of an esterifying agent and the reduction of the oxidized waxes to polyhydroxy-waxes is set forth in U.S. Pat. No. 3,425,930. The esterification agent useful in the oxidation is set forth as including aliphatic or aromatic organic acids or anhydrides thereof.

SUMMARY OF THE INVENTION

It now has been found that an ester can be produced in useful yield, without difficulty in separating the ester from the water used to remove the catalyst from the esterification of an unsweated, oil containing wax oxidate, by contacting the unsweated wax oxidate with an alcohol and with an organic sulfonic acid under effective esterifying temperature and pressure conditions. It has been found that water will rapidly and easily remove the organic sulfonic acid catalyst from the reaction mixture without emulsification or difficulties in separating the ester layer and the organic sulfonic acid containing water layer. The new process results in a clean separation of the acid containing water layer from the ester containing organic layer while permitting the use of unsweated, oil containing wax as a feedstock to the process. In this process there is no need to add other materials to cause the rapid and substantially complete separation of the layers.

PREFERRED EMBODIMENTS OF THE INVENTION

In a preferred embodiment of the invention an unsweated wax oxidate is esterified with a low molecular weight aliphatic alcohol using an aliphatic or aromatic organic sulfonic acid as a catalyst under effective temperature and pressure conditions. The catalyst is separated from the resulting ester by contacting the reaction mixture with water which dissolves the sulfonic acid. The acid containing water layer then easily and rapidly separates from the ester layer. The rapid separation of the two layers permits the complete separation of the ester from the water and the sulfonic acid catalyst.

Useful organic sulfonic acids are aliphatic and aromatic sulfonic acids which include alkyl, and alkylaryl sulfonic acids. Examples of such acids include methane sulfonic acid, benzene sulfonic acid, p-toluene sulfonic acid, and ethane sulfonic acid. Presently, the most preferred sulfonic acid is methane sulfonic acid which is readily commercially available, has good catalytic activity and is relatively safe to handle in a commercial process. The sulfonic acid catalyst can comprise from about 0.01 to about 1 percent by weight of the reaction mixture and preferably from about 0.02 percent to about 0.8 percent by weight can be used.

Wax oxidates useful in the esterification process of the present invention can be conventionally prepared such as by conventional air oxidation of unsweated waxes. For example, in one conventional process, a molten hydrocarbon wax charge is subject to agitation and gaseous oxygen in contact with the molten wax. Catalysts such as permanganate can be used.

Alcohols useful in the esterification process include mono and polyhydric alcohols. The alcohols preferably are lower weight aliphatic alcohols such as those having from 1 to about 10 carbon atoms, such alcohols include methanol, ethanol, propanol, etc. The alcohol chosen will depend on the desired use of the ester and the desired reaction conditions.

Oils are defined herein as hydrocarbons which are liquid above about 10° C.

Waxes useful in the process of the present invention are those derived from petroleum by conventional separation procedures such as chilling or solvent extraction. Useful waxes can contain from about 18 to about 40 carbon atoms. Such waxes can include paraffin, crystalline, and microcrystalline waxes. The waxes can contain upwards of 15 percent, generally about 5 to 15 percent by weight oil, and can melt at a temperature between about 25° about 95° C., preferably 40° to 60° C. The wax preferably has a minimum flash point COC (Cleveland Open Cup Method) of about 200° C., has an oil content of no more than 15 percent by weight, has a color by the ASTM method of 2.0 max, and has a kinematic viscosity at 100° C. of between about 2 and 5 centiStokes.

The preferred wax oxidate is formed from the air oxidation of the preferred wax and has a melting point between about 40° and 55° C., a saponification number between 125 and 175, a flash point COC of 135° C. minimum, a neutralization number between 70 and 95, a color by the ASTM method of 5 maximum, an ash content of 0.05 percent by weight maximum and a kinematic viscosity at 100° C. of between 4 and 10 centi-Stokes.

The esterification reaction can be run at any effective temperature and pressure. Generally, such temperatures are from about 40° C. to the reflux temperature of the mixture which is generally 80° to 90° C. depending on the materials used. With the preferred materials, the reflux temperature is about 80° C. Generally, the preferred pressure is atmospheric; however, pressures higher than atmospheric can be used.

Generally, an excess of the alcohol on a molar basis is used, since an excess of alcohol is needed to drive the equilibrium of the esterification reaction towards ester formation. However, too large of an excess of alcohol leads to a low yield and the loss of starting material. One skilled in the art can readily determine a proper material balance for the starting materials to achieve the highest yield of ester. Generally, during the preferred process wherein the materials are heated to reflux, any materials which do pass through the reflux condenser are condensed and returned to the reaction mixture and not removed.

After the esterification has proceeded to a desired point, which is generally determined by the neutralization number of the reaction product which is determined as the number of milligrams of potassium hydroxide needed to neutralize one gram of product, the reaction is stopped and the reaction mixture allowed to cool. The alcohol is separated from the reaction mixture, preferably by distillation and most preferably by distillation under vacuum.

In the preferred process of the present invention, the acid catalyst and water soluble reaction products are separated from the reaction mixture by water washing. In the preferred process of the present invention, wherein an organic sulfonic acid is used as a catalyst with unsweated wax, the water layer containing the organic sulfonic acid catalyst readily separates from the ester after the washing step. This rapid and substantially complete separation permits the ester to be rapidly and cleanly separated from the water and sulfonic acid catalyst. Previously, only sweated oxidated waxes were usable as feedstocks for the esterification process, since when unsweated oxidated waxes were used, the water washing step resulted in an emulsion which was difficult to break and which made it difficult to separate the ester from the water. In the process of the present invention with the use of organic sulfonic acids instead of the previously used sulfuric acid, no such problems were encountered.

The invention will be better understood from the following examples which are merely illustrative and not meant to limit the invention in any way.

EXAMPLE I

Into a large reactor was pumped about 4200 liters of methanol, about 8,100 liters of unsweated wax oxidate having properties within the ranges set forth in Table I, and about 23 liters of methane sulfonic acid.

TABLE I

| Flash Point (Cleveland Open Cup) | 200° C. minimum |
| Melting Point | 46° C. to 52° C. |
| Oil Content Wt. % | 15% maximum |
| Viscosity Kinematic @ 100° C. | 2.86 to 4.7 cSt |

The reactor was then heated to reflux. This occurred at a temperature of between about 70° and 77° C. The reflux was continued until the reaction mixture required no more than about 11 milligrams of potassium hydroxide per gram of reaction mixture to produce a neutral solution. This took approximately 11 hours.

After the desired neutralization number was reached, the methanol was stripped from the reactor at about 95° C. After the methanol was stripped from the reaction mixture, the reaction mixture was allowed to cool and then washed with about 4500 liters of water. The reaction mixture was then allowed to settle for several hours. The water containing the methane sulfonic acid catalyst was then drawn off from the tank. The reaction mixture was then subjected to a vacuum and heated to a temperature of between about 95° and 105° C. until there was less than 1 percent water in the reaction mixture. The ester was then usable for formulation in various products.

The yield of ester was about 7050 liters which was about 87 volume percent yield. The chemical and physical properties of the resulting ester are set forth in Table II below.

TABLE II

| Flash (COC) | 170° C. |
| Color ASTM | 3.5 |
| Melting Point | 43° C. |
| Kinematic Viscosity @ 100° C. | 4.8 cSt |
| Saponification Value | 142 |
| Neutralization Number | 11 |

EXAMPLE II

A reaction mixture was formed as in Example I with about 9000 liters of unsweated wax oxidate, about 4200 liters of methanol and about 20 liters of methane sulfonic acid. The reaction mixture was refluxed for about 3¼ hours until the reaction mixture required about 11 milligrams of potassium hydroxide per gram of reaction mixture for neutralization. The methanol was stripped and the product washed and separated as in Example I. This reaction yielded about 7920 liters of ester which was about 88 percent by volume yield. The physical and chemical characteristics of the unsweated wax oxide and the resulting ester were similar to those of Example I.

EXAMPLE III

A reaction mixture was made as in Example II and was refluxed at a temperature of about 68° C. for about 7 hours. The reaction product was treated as in Examples I and II and yielded an ester of about 7740 liters which was about a 86 percent by volume reaction yield. The physical and chemical characteristics of the unsweated wax oxidate and the resulting ester were similar to those of Example I.

The above examples are for illustrative purposes only, changes and modifications can be made by one skilled in the art and remain within the present invention which is set forth in the following claims.

What is claimed is:

1. A method for esterifying an unsweated, oil containing wax oxidate comprising the steps of contacting said unsweated wax oxidate; said wax oxidate formed from the air oxidation of a petroleum derived wax and said wax oxidate having a melting point between 40° C. and 55° C., a saponification number between 125 and 175, a flash point COC of 135° C. minimum, a neutralization number between 70 and 95, a maximum ASTM color of 5, a maximum ash content of 0.05 percent by weight and a kinematic viscosity at 100° C. of 4 to 10 centiStokes, with an alcohol and with an organic sulfonic acid under effective esterifying temperature and pressure conditions; washing said organic sulfonic acid with water from said resulting reaction mixture; and separating the acid containing water layer and the ester containing organic layer.

2. The method of claim 1 and further comprising the step of removing unreacted alcohol from said reaction mixture.

3. The method of claim 1 wherein said organic sulfonic acid comprises an aliphatic or aromatic sulfonic acid.

4. The method of claim 3 wherein said organic sulfonic acid is selected from the group consisting of methane sulfonic acid, benzene sulfonic acid, p-toluene sulfonic acid and ethane sulfonic acid.

5. The method of claim 1 wherein said sulfonic acid catalyst comprises from about 0.1 to about 1 percent by weight of the reaction mixture.

6. The method of claim 1 wherein said unsweated wax oxidate contains between about 5 and 15 percent by weight oil.

7. The method of claim 1 wherein said alcohol comprises a lower weight aliphatic alcohol having from 1 to about 10 carbon atoms.

8. The method of claim 1 wherein said wax oxidate has from about 18 to about 40 carbon atoms.

9. A method for esterifying an unsweated, oil containing oxidate; said wax oxidate formed from the air oxidation of a petroleum derived wax and said wax oxidate having a melting point between 40° C. and 55° C., a saponification number between 125 and 175, a flash point COC of 135° C. minimum, a neutralization number between 70 and 95, a maximum ASTM color of 5, a maximum ash content of 0.05 percent by weight and a kinematic viscosity at 100° C. of 4 to 10 centiStokes; comprising the steps of containing said unsweated wax oxidate having from about 5 to 15 percent by weight oil with methanol and methane sulfonic acid; heating the mixture at an effective esterification temperature and pressure; removing unreacted methanol from the reaction mixture; washing the reaction mixture with water; and separating the organic ester containing layer and the methane sulfonic acid containing water layer, whereby the separation of the two layers is substantially complete without the addition of the other materials.

10. The method of claim 11 wherein said methane sulfonic acid catalyst comprises from about 0.01 to about 1 percent by weight of the reaction mixture.

11. The method of claim 9 wherein said wax oxidate has from about 18 to about 40 carbon atoms.

* * * * *

UNITED STATES PATENT AND TRADEMARK OFFICE
CERTIFICATE OF CORRECTION

PATENT NO. : 4,548,754

DATED : October 30, 1985

INVENTOR(S) : Frederick Frank Day, William Joseph Powers, III, Eric DeWitt Ewen and Gerald Lee Piper It is certified that error appears in the above-identified patent and that said Letters Patent is hereby corrected as shown below:

Claim 9, lines 3 and 4 "containing oxidate" should read --containing wax oxidate--.

Claim 10, line 23, "0.01" should read --0.1--.

Signed and Sealed this

Seventh Day of January 1986

[SEAL]

Attest:

Attesting Officer

DONALD J. QUIGG

Commissioner of Patents and Trademarks